Nov. 8, 1955 E. S. BOERNER Plant Pat. 1,434
ROSE PLANT
Filed Feb. 7, 1955
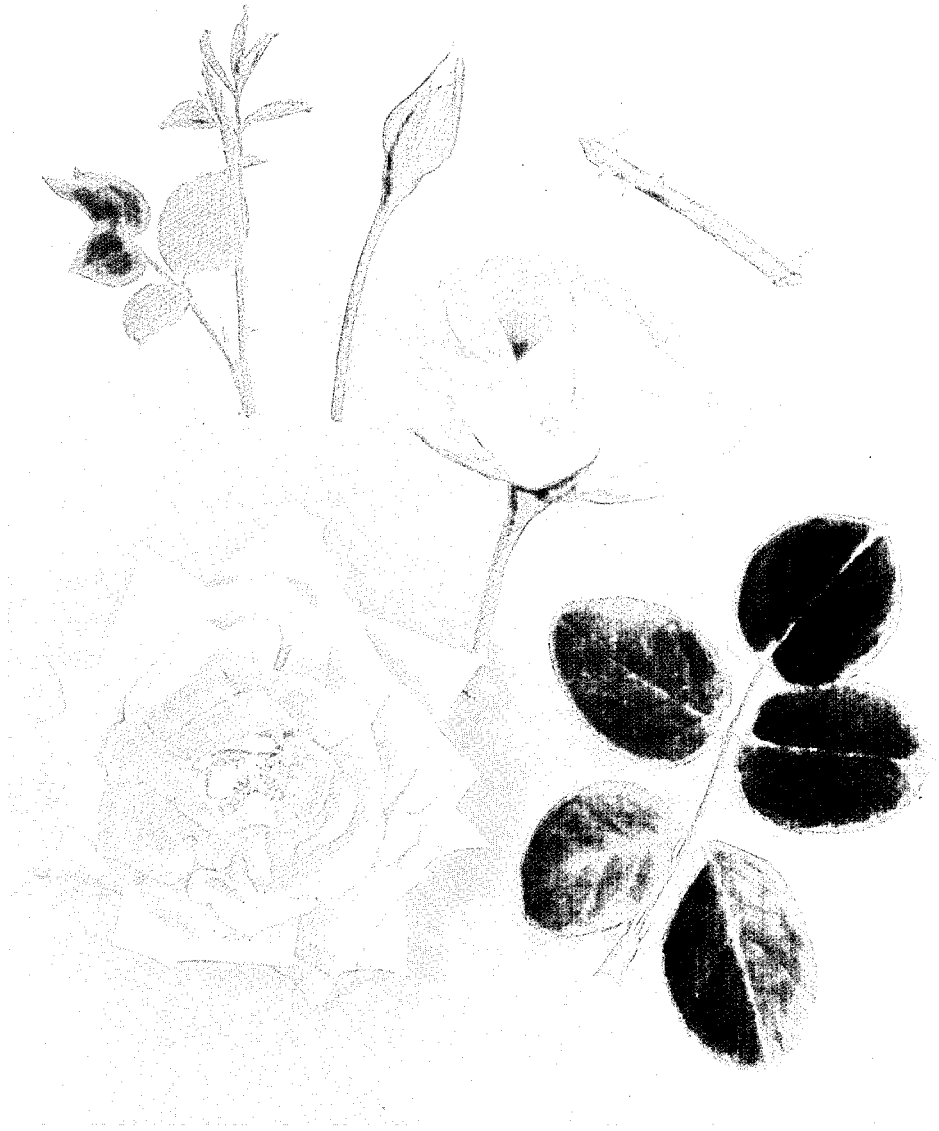
Inventor.
E. S. Boerner
By: Robb & Robb
Attorneys.

United States Patent Office

Plant Pat. 1,434
Patented Nov. 8, 1955

1,434

ROSE PLANT

Eugene S. Boerner, Newark, N. Y., assignor to Jackson & Perkins Company, Newark, N. Y., a corporation of New York Application February 7, 1955, Serial No. 486,747

1 Claim. (Cl. 47—61)

The present invention relates to a new and distinct variety of rose plant of the hybrid tea class, which was originated by me by crossing the variety "Grey Pearl" (Plant Patent No. 680) with the variety "Lavender Pinocchio" (Plant Patent No. 947).

The primary objective of this breeding was to produce a new rose variety which bears flowers of the hybrid tea form, but in a new color. This objective was fully achieved, as evidenced by the following unique combination of characteristics which are outstanding in my new variety:

(1) The very heavily leafed plant;

(2) Rugged foliage of a deep dull yellow green color;

(3) The perfect shape of the half-open buds, and their habit of unfolding very slowly;

(4) The unique and distinctive color of the flowers which are best described as Persian lilac in general color tonality; and (5) The unique and distinctive combination of colors of the flower petals which, on the reverse surface, are White with their outer edges light vinaceous lilac and with the lower half of the petals overcast with Colonial buff, and which, on the inner surface of the petals, are Rhodonite pink, lightly overcast with Rocellin purple, giving an overall impression of a lavender lilac general color tonality when the flowers open.

The foregoing characteristics and distinctions definitely differentiate my new variety from its parents, as well as from all other varieties of its class, and asexual reproduction of the new variety by budding, as performed at Newark, New York, and also at Pleasanton, California, shows that these characteristics and distinctions come true to form and are established and transmitted through succeeding propagations.

The accompanying drawing shows typical specimens of the foliage, stems and flower of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Grey Pearl."
*Pollen parent.*—"Lavender Pinocchio."
Classification:
*Botanic.*—Hybrid tea.
*Commercial.*—Hybrid tea.

FLOWER (Observations made from specimens grown in a garden at Newark, New York, in the early morning, and in the early part of the month of July.)

Blooming habit: Recurrent—continuous.
Bud:
*Size.*—Medium.

*Form.*—From ovoid to pointed; is not affected by wet or hot weather.
*Color.*—When sepals first divide—Deep Purplish Vinaceous, Plate 44. When petals begin to unfurl—Marguerite Yellow, Plate 30. When half blown: inside of petals—Vinaceous Lilac, plate 44, lightly overcast with Vinaceous Purple, Plate 38; reverse of petals—Marguerite Yellow, Plate 30, lightly overcast with Pale Persian Lilac, Plate 38 on the edges of the petal.
*Sepals.*—Slightly branched; curl back when petals begin to unfurl.
Color—inside—Biscay Green, Plate 17; outside—Light Cress Green, Plate 31.
*Calyx:*
Color—Spinach Green, Plate 5.
Shape—pear.
Size—small.
Aspect—smooth.
Odor when rubbed—none.
*Peduncle:*
Length—medium.
Aspect—smooth.
Strength—erect; slender.
Color—Parrot Green, Plate 6.
*Opening.*—Opens up well; is not affected by adverse weather conditions.
Bloom:
*Size.*—Medium. Average size when fully expanded—4½ inches.
*Borne.*—Singly and several together.
*Stems.*—Medium length; normal strength.
*Form (when first open).*—High center. Permanence—retains its form to the end.
*Petalage.*—Double (full but open center). Number of petals under normal conditions—from 30 to 35.
*Color:*
Center of flower—Persian Lilac, Plate 38, lightly overcast with Vernonia Purple, Plate 38.
Outer petals—Pale Laelia Pink, Plate 38.
Base of petals (aiglet)—Chartreuse Yellow, Plate 31.
Inside of petals—Rhodonite Pink, Plate 38, lightly overcast with Rocellin Purple, Plate 38.
Reverse of petals—White, Plate 53, with outer edges of petals Light Vinaceous-Lilac, Plate 44, and with the lower half of the petals overcast with Colonial Buff, Plate 30.
General tonality from a distance—Persian Lilac, Plate 38.
*Discoloration:*
General tonality at end of first day—Persian Lilac, Plate 38, with a light overcast of Vernonia Purple, Plate 38.
Second day—Persian Lilac, Plate 38.
Third day—Rhodonite Pink, Plate 38, lightly overcast with Persian Lilac, Plate 38.
*Petals:*
*Texture.*—Thick; is not affected by wet or hot weather.
*Appearance.*—Inside—satiny; outside—shiny.
*Form.*—Oval.
*Arrangement.*—Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—long; as cut flower—long.

GENITAL ORGANS

Stamens, anthers: Medium size; many; regularly arranged around styles.
*Color.*—Antimony Yellow, Plate 15.
Stamens, filaments (threads): Medium length.
*Color.*—Strontian Yellow, Plate 16.
Pollen:
*Color.*—Light Buff, Plate 15.
Styles: Bunched; uneven length; medium length; thin.
Stigmas:
*Color.*—Martius Yellow, Plate 4.
Ovaries: All enclosed in calyx.
Hips: None.
Seeds: None.

PLANT

Form: Bush.
Growth: Vigorous; upright; branching.
Foliage: 5 to 7 leaflets.
*Size.*—Medium.
*Quantity.*—Abundant.
*Color*:
New foliage—upper side—Yellowish Oil Green, Plate 5, lightly overcast with Carmine, Plate 1 on the outer edges of the petals, and with serrations of Carmine, Plate 1; under side—Deep Hellebore Red, Plate 38, with mid-rib of Yellowish Oil Green, Plate 5.
Old foliage—upper side—Deep Dull Yellow Green, Plate 32, with center of leaf lightly overcast with Kronberg's Green, Plate 31; under side—Light Grape Green, Plate 41.
*Shape.*—Oval pointed.

*Texture.*—Upper side—glossy; under side—smooth.
*Ribs and veins.*—Prominent.
*Edge.*—Serrated (saw-toothed).
*Serration.*—Both double and single; small.
*Leaf stem.*—Color—Jade Green, Plate 31. Under side—Prickles.
*Stipules.*—Short; slightly bearded.
Wood:
*New wood.*—Color—Apple Green, Plate 17. Bark—smooth.
*Old wood.*—Color—Forest Green, Plate 17. Bark—smooth.
Thorns:
*Thorns.*—Quantity—on main stalks from base—ordinary; on laterals from stalk—ordinary.
Form—flat base; medium length; straight.
Color (when young)—Begonia Rose, Plate 1.
Position—irregular.
*Prickles.*—Quantity—on main stalks—none; on laterals—none.
*Short needles.*—Quantity—on main stalks—none; on laterals—none.

I claim:

A new and distinct variety of rose plant of the hybrid tea class, substantially as herein shown and described, characterized particularly as to novelty by its very heavily leafed plant, its rugged foliage of deep dull yellow green color, the perfect shape of its half-open buds and their habit of unfolding very slowly, and the unique and distinctive color combination of the inner and outer surfaces of the flower petals, giving an overall impression of a lavender lilac general color tonality.

No references cited.